US00PP19103P2

(12) United States Plant Patent
Murakami

(10) Patent No.: US PP19,103 P2
(45) Date of Patent: Aug. 19, 2008

(54) ***NIEREMBERGIA* PLANT NAMED 'SUNNIPARIHO'**

(50) Latin Name: *Nierembergia hybrida*
Varietal Denomination: Sunnipariho

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 1 day.

(21) Appl. No.: 11/633,116

(22) Filed: Dec. 1, 2006

(51) Int. Cl.
*A01H 5/00* (2006.01)

(52) U.S. Cl. ..... Plt./459
(58) Field of Classification Search ..... Plt./263, Plt./459
See application file for complete search history.

*Primary Examiner*—Howard J. Locker
(74) *Attorney, Agent, or Firm*—C. A. Whealy

(57) ABSTRACT

A new and distinct cultivar of *Nierembergia* plant named 'Sunnipariho', characterized by its compact, upright and mounding plant habit; vigorous growth habit; freely branching habit; large white-colored flowers; freely and continuous flowering habit; and good garden performance.

1 Drawing Sheet

Botanical designation: *Nierembergia hybrida.*
Cultivar denomination: 'Sunnipariho'.

BACKGROUND OF THE INVENTION

The present invention relates to a new and distinct cultivar of *Nierembergia,* botanically known as *Nierembergia hybrida* and hereinafter referred to by the name 'Sunnipariho'.

The new *Nierembergia* is a product of a planned breeding program conducted by the Inventor in Shiga, Japan. The objective of the breeding program was to create new compact *Nierembergia* cultivars with attractive flower coloration.

The new *Nierembergia* originated from a cross-pollination made by the Inventor during the summer of 2003, in Shiga, Japan, of a proprietary selection of *Nierembergia hybrida* identified as code number NS1, not patented, as the female, or seed, parent with a proprietary selection of *Nierembergia hybrida* identified as code number NWL176, not patented, as the male, or pollen, parent. The new *Nierembergia* was discovered and selected by the Inventor as a single flowering plant within the progeny of the stated cross-pollination in a controlled environment in Shiga, Japan.

Asexual reproduction of the new *Nierembergia* by vegetative cuttings in a controlled environment in Shiga, Japan since October, 2005, has shown that the unique features of this new *Nierembergia* are stable and reproduced true to type in successive generations.

SUMMARY OF THE INVENTION

The cultivar Sunnipariho has not been observed under all possible environmental conditions. The phenotype may vary somewhat with variations in environment and cultural practices such as temperature and light intensity without, however, any variance in genotype.

The following traits have been repeatedly observed and are determine to be the unique characteristics of 'Sunnipariho'. These characteristics in combination distinguish 'Sunnipariho' as a new and distinct cultivar of *Nierembergia:*

1. Compact, upright and mounding plant habit.
2. Vigorous growth habit.
3. Freely branching habit.
4. Large white-colored flowers.
5. Freely and continuous flowering habit.
6. Good garden performance.

Compared to plants of the parent selections, plants of the new *Nierembergia* are more freely branching and flower earlier.

Plants of the new *Nierembergia* can also be compared to plants of the cultivar Sunniparisobu, disclosed in U.S. Plant Pat. No. 16,394. In side-by-side comparisons conducted in Shiga, Japan, plants of the new *Nierembergia* and the cultivar Sunniparisobu differed in the following characteristics:

1. Plants of the new *Nierembergia* were shorter but more outwardly spreading than plants of the cultivar Sunniparisobu.
2. Plants of the new *Nierembergia* had shorter internodes than plants of the cultivar Sunniparisobu.
3. Plants of the new *Nierembergia* were more freely branching than plants of the cultivar Sunniparisobu.
4. Plants of the new *Nierembergia* had narrower leaves than plants of the cultivar Sunniparisobu.
5. Plants of the new *Nierembergia* flowered earlier than plants of the cultivar Sunniparisobu.
6. Plants of the new *Nierembergia* had larger flowers than plants of the cultivar Sunniparisobu.
7. Plants of the new *Nierembergia* and the cultivar Sunniparisobu differed in flower color.

BRIEF DESCRIPTION OF THE PHOTOGRAPHS

The accompanying colored photographs illustrate the overall appearance of the new *Nierembergia,* showing the colors as true as it is reasonably possible to obtain in colored reproductions of this type. Colors in the photographs may differ slightly from the color values cited in the detailed botanical description which accurately describe the colors of the new *Nierembergia*.

The photograph at the top of the sheet comprises a side perspective view of a typical flowering plant of 'Sunnipariho' grown in a container.

The photograph at the bottom of the sheet is a close-up view of typical flowers of 'Sunnipariho'.

DETAILED BOTANICAL DESCRIPTION

The aforementioned photographs and following observations, measurements and values describe plants grown in Shiga, Japan, under commercial practice during the spring and summer in an outdoor nursery with day temperatures averaging 21° C. and night temperatures averaging 14° C. After planting, plants had been growing for about four months when the photographs and description were taken. In the following description, color references are made to The Royal Horticultural Society Colour Chart, 2001 Edition, except where general terms of ordinary dictionary significance are used.

Botanical classification: *Nierembergia hybrida* cultivar Sunnipariho.

Parentage:

*Female, or seed, parent.*—Proprietary selection of *Nierembergia hybrida* identified as code number NS1, not patented.

*Male, or pollen, parent.*—Proprietary selection of *Nierembergia hybrida* identified as code number NWL176, not patented.

Propagation:

*Type.*—By vegetative cuttings.

*Time to initiate roots.*—About two weeks at 20° C. to 25° C.

*Time to produce a rooted young plant roots.*—About 35 days at 20° C. to 25° C.

*Root description.*—Fine, fibrous; white in color.

*Rooting habit.*—Freely branching.

Plant description:

*Plant form/habit.*—Compact, upright and mounded plant habit; outwardly spreading; vigorous growth habit. Freely branching habit; pinching enhances branching potential.

*Plant height.*—About 23 cm.

*Plant width (spread).*—About 38.6 cm.

*Lateral branches.*—Length: About 13.8 cm. Diameter: About 0.8 mm. Internode length: About 6 mm. Strength: Strong. Texture: Pubescent. Color: 147B.

Foliage description:

*Arrangement.*—Alternate, simple; sessile.

*Length.*—About 3.3 cm.

*Width.*—About 7 mm.

*Shape.*—Narrowly elliptic.

*Apex.*—Acute.

*Base.*—Obtuse.

*Margin.*—Entire.

*Texture, upper and lower surfaces.*—Pubescent.

*Venation pattern.*—Pinnate.

*Color.*—Developing leaves, upper and lower surfaces: 137C. Fully expanded leaves, upper surface: 137B; venation, 145A. Fully expanded leaves, lower surface: 137A; venation, 147A.

Flower description:

*Flower type/habit.*—Single salverform flowers; flowers face mostly upright. Freely flowering habit with about 60 flowers developing per plant.

*Fragrance.*—None detected.

*Natural flowering season.*—Continuously flowering from spring to late autumn in Shiga, Japan. Flowers not persistent.

*Postproduction longevity.*—Flowers last about five days on the plant.

*Flower buds.*—Height: About 2.7 cm. Diameter: About 4.9 mm. Shape: Clavate. Color: 112D.

*Flower diameter.*—About 4 cm.

*Flower depth.*—About 3.1 cm.

*Petals.*—Quantity per flower: Typically five in a single whorl; petals fused. Length: About 1.6 cm. Lobe width: About 1.7 cm. Tube length: About 1.9 cm. Tube diameter: About 0.9 mm. Shape: Roughly spatulate. Apex: Obtuse to rounded. Margin: Crenate; undulate. Texture, upper and lower surfaces: Smooth, glabrous. Texture, tuber; Pubescent. Color: Developing and fully expanded petals, upper surface: 155C; towards the center, 5B. Developing and fully expanded petals, lower surface: 155C. Throat: 150D. Tube: 10D.

*Sepals.*—Quantity per flower: Typically five in a single whorl, fused at base; star-shaped calyx. Length: About 7 mm. Width: About 2.4 mm. Shape: Lanceolate. Apex: Acute. Margin: Entire. Texture, upper and lower surfaces: Smooth, glabrous. Color, upper surface: 137B. Color, lower surface: 138B.

*Peduncles.*—Length: About 1.3 mm. Diameter: About 0.6 mm. Texture: Pubescent. Color: 137B.

*Reproductive organs.*—Stamens: Quantity per flower: Typically five. Stamen length: About 5 mm. Anther shape: Globose. Anther size: About 2 mm to by 2 mm. Anther color: 10A. Pollen amount: Moderate. Pollen color: 12B. Pistils: Quantity per flower: One. Pistil length: About 2.4 cm. Stigma shape: Reniform. Stigma color: 144B. Style color: 145B. Ovary color: 144A.

*Seed/fruit.*—Seed and fruit development have not been observed.

Disease/pest resistance: Plants of the new *Nierembergia* have not been noted to be resistant to pathogens and pests common to *Nierembergia*.

Garden performance: Plants of the new *Nierembergia* have been observed to have good garden performance and tolerate rain, wind and temperatures from about −8° C. to about 35° C.

It is claimed:

1. A new and distinct *Nierembergia* plant named 'Sunnipariho' as illustrated and described.

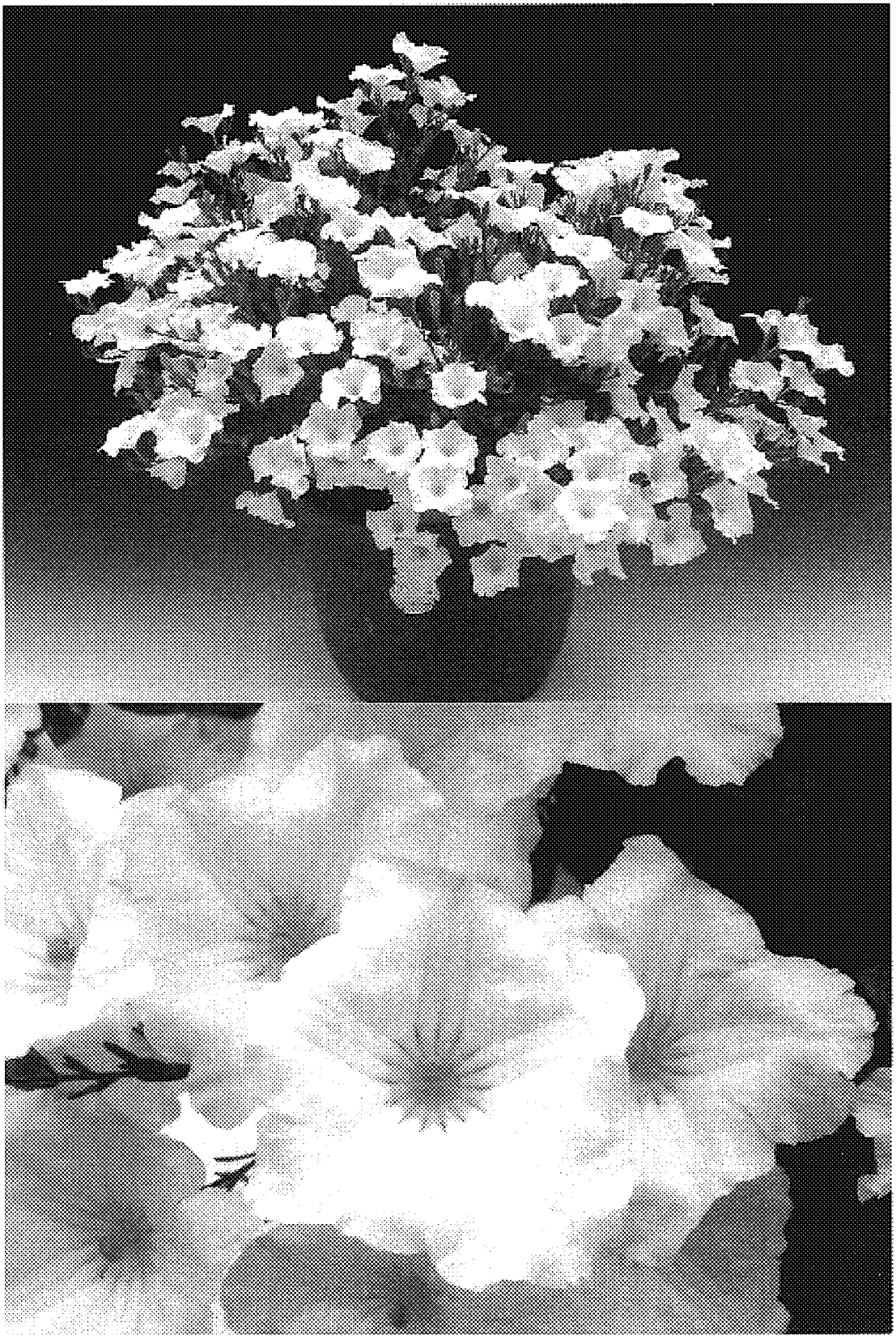

* * * * *